(12) United States Patent
Widlund et al.

(10) Patent No.: US 6,375,646 B1
(45) Date of Patent: Apr. 23, 2002

(54) ABSORBENT PANTS-TYPE DIAPER

(75) Inventors: Urban Widlund, Mölnlycke; Gunilla Hedlund, Ljungskile; Robert Kling, Skene, all of (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 08/295,874

(22) PCT Filed: Mar. 1, 1993

(86) PCT No.: PCT/SE93/00176

§ 371 Date: Sep. 6, 1994

§ 102(e) Date: Sep. 6, 1994

(87) PCT Pub. No.: WO93/17648

PCT Pub. Date: Sep. 16, 1993

(30) Foreign Application Priority Data

Mar. 4, 1992 (SE) .............................. 9200663

(51) Int. Cl.$^7$ ................................ A61F 13/15
(52) U.S. Cl. .................. 604/385.3; 604/385.22
(58) Field of Search .................. 604/385.1, 385.2, 604/358, 394, 396, 385.22, 385.29, 385.3

(56) References Cited

U.S. PATENT DOCUMENTS

| | | | | |
|---|---|---|---|---|
| 2,748,772 A | * | 6/1956 | Titone et al. ............... | 604/396 |
| 3,424,162 A | * | 1/1969 | Perrsviciri .................. | 604/396 |
| 4,319,572 A | * | 3/1982 | Widlund et al. ........... | 604/385.2 |
| 4,615,695 A | * | 10/1986 | Couper ..................... | 604/385.2 |
| 4,756,709 A | * | 7/1988 | Stevens ..................... | 604/385.2 |
| 4,762,521 A | * | 8/1988 | Roessler et al. ........... | 604/385.2 |
| 4,850,989 A | * | 7/1989 | Villez ........................ | 604/385.2 |
| 4,909,804 A | * | 3/1990 | Douglas .................... | 604/385.2 |
| 4,940,464 A | * | 7/1990 | Van Gompel et al. ..... | 604/396 |
| 4,968,312 A | * | 11/1990 | Khan ........................ | 64/385.1 |
| 5,004,466 A | * | 4/1991 | Uda et al. ................... | 604/385.2 |

FOREIGN PATENT DOCUMENTS

| | | | | |
|---|---|---|---|---|
| EP | 0 357 298 | | 3/1990 | |
| EP | 0 404 648 | | 12/1990 | |
| EP | 0 456 885 | | 11/1991 | |
| EP | 0 460 467 | | 12/1991 | |
| EP | 0 528 282 | | 2/1993 | |
| ES | 222874 | | 8/1976 | |
| ES | 277230 | | 2/1984 | |
| ES | 288654 | | 8/1985 | |
| ES | 289369 | | 10/1985 | |
| ES | U 8701780 | | 5/1987 | |
| ES | U 8902797 | | 9/1989 | |
| ES | U 9202481 | | 8/1992 | |
| ES | U 9300525 | | 3/1993 | |
| GB | 2253131 | * | 9/1992 | ............ 604/385.2 |
| JP | 3195555 | * | 8/1991 | ............ 604/385.2 |
| JP | 3205053 | * | 9/1991 | ............... 604/396 |
| JP | 4354948 | * | 12/1992 | ............... 604/394 |

* cited by examiner

*Primary Examiner*—Dennis Ruhl
(74) *Attorney, Agent, or Firm*—Young & Thompson (57) ABSTRACT

A disposable, absorbent pants-type diaper includes a front-part (1), a back-part (2), a crotch-part (3) between the front and back parts (1, 2), at least two side-closure parts (12, 13) which mutually join parts of the side-edges (4, 5) of respective front and back parts, so that the pants will present a waist opening (9) and two leg openings (10, 11). The diaper pants further include an elongated absorbent pad (14), an inner casing layer (15), and an outer casing layer (16). At least one of the respective front and back parts (1, 2) has at least one elastically stretchable region (29, 30). The crotch-part (3) is essentially non-stretchable in relation to the stretchable region (29, 30). At least one of respective end-parts (17, 18) of the absorbent pad (14) is disposed within one of the elastically stretchable regions (29, 30), while the center-part (19) of the absorbent pad is disposed within the relatively non-stretchable crotch-part (3) of the pants.

28 Claims, 2 Drawing Sheets

ABSORBENT PANTS-TYPE DIAPER

FIELD OF THE INVENTION

The present invention relates to an absorbent pants-type diaper of the kind which is intended for one-time use only and which comprises a front-part, a back-part, a crotch-part that extends between said front and back parts, at least two side-closure parts which mutually join parts of the side-edges of the front and back parts such that the diaper will include a waist opening and two leg openings. The diaper further comprises an elongated absorbent pad having a front and a rear end-part and a centre-part located therebetween, an inner casing layer placed on that side of the pad which is intended to face towards the wearer in use and an outer casing layer, or backing sheet, placed on the other side of the absorbent pad.

BACKGROUND OF THE INVENTION

In the case of diaper-wearing children who are in a transition period in which they learn to control the discharge of urine and are weaned-off the use of conventional diapers and trained to perform their bodily evacuative functions on the toilet, there is a need for an absorbent article which while absorbing body fluids will, at the same time, resemble a pair of conventional underpants. Absorbent pants-type diapers which are intended to be worn during such weaning or training periods are often referred to as training pants. One significant difference between an absorbent pants-type diaper and a conventional diapers is the manner in which they are intended to be worn in daily use. Absorbent pants-type diapers shall be capable of being taken-off and put-on repeatedly in the same manner as a pair of conventional underpants, until the wearer urinates in the pants-type diaper, wherewith the urine is absorbed by the pants, in precisely the same manner as a diaper, so that the pants-type diaper will continue to function as underpants in a user-safe fashion, until there is time and the opportunity to replace the soiled pants-type diaper with a fresh diaper. The soiled diaper can then be thrown away. The pants-type diaper will preferably be designed to give the wearer a decisive feeling that he/she is wearing a garment which is different from the diapers earlier used, and so that the wearer is able to remove the diaper easily, for instance when going to the toilet. In this latter respect, it is important, among other things, to give the pants-type diaper the form of a pair of pants, i.e. an article which has a waist opening and two leg openings, and not the form of a diaper that has fastener tabs or the like for joining the back-part of the diaper to the front-part thereof when putting-on the diaper. This latter procedure is highly complicated and extremely difficult for a child, or even an adult person, to achieve by himself/herself. In the case of known disposable pants-type diapers, or training pants, it has also been proposed to include an outer casing layer which is made of a textile-like, disposable material, such as to assimilate a genuine textile material to the greatest possible extent, so that primarily adult wearers are relieved of the psychologically negative association with napkins that is given unavoidably by the plastic outer casing sheets or layers characteristic of disposable diapers.

However, the requirement for pants-type diapers to resemble a pair of underpants creates a number of problems. The fastener tabs which function to secure diapers around the wearer's body also fulfil the important role of supporting the extra load occasioned by the not inconsiderable amount of fluid that is delivered to the absorbent pad. As a result of the fastener tabs, the waist part of the diaper, i.e. that part around the wearer's waist which is formed when the fastener tabs are secured to the diaper, becomes rigid and unyielding to a certain extent in those parts where the fastener tabs are attached. The waist parts of the diaper are thus prevented from stretching to an extent beyond that permitted by the material in the waist part of the diaper and in the rigid or inflexible fastener tabs. Naturally, the extent to which the waist part will yield or give varies among known fastener tabs, although the fastener tabs will normally place a limit on the extent to which the waist parts of the diapers can stretch. Consequently, the diapers remain safely in position on the wearer, even when the absorbent pad has been filled with urine, at least provided that the fastener tabs are secured tightly enough. This waist-tightening mechanism is not found in pants-type diapers, since they lack the provision of fastener tabs. Thus, the pants-type diapers are held-up around the wearer's waist totally through the agency of the diaper casing layers or sheets and any elastication that may be provided. When considering that pants-type diapers are intended to be used by diaper-wearing children from about two to four years of age, or by older children who suffer from incontinence, or even by adults, it will be understood that the quantities of fluid that are liable to be absorbed by the absorbent pad can be quite considerable and therewith also the weight that acts on the diapers. Consequently, high demands are placed on the construction of such pants-type diapers with regard to their load-supporting capacity, so that the pants-type diapers will not fall down the legs of the wearer under the weight of the fluid absorbed.

In addition to being able to support the weight of the absorbed fluid, the pants-type diaper shall also fit snugly around the wearer's body. Furthermore, the diaper shall be sufficiently elastic or stretchable to enable it to be readily pulled on and off.

The U.S. Pat. No. 4,205,679 teaches an absorbent pants-type diaper which is constructed from one or more layers of stretchable non-woven fabric. According to one preferred embodiment, both the outer and the inner casing sheet of the pants-type diaper is made of a micro-corrugated or micro-pleated non-woven material which in the manufacture of the material can be made stretchable in two directions, i.e. in the machine direction and in a direction transversely thereto. Elastic elements, for instance in the form of an elastic natural-rubber bands or ribbons are also mounted along the end-edges of the diaper, i.e. at its waist opening.

European Patent Application EP 0 320 991 A2 teaches an absorbent pants-type diaper which includes a central absorbent unit and two side-pieces which are joined with the absorbent unit along parts of the side-edges thereof. The side-pieces include elastic side-parts. In addition, elastic elements may be mounted to provide waist and leg elastic in certain embodiments. On the other hand, none of the casing sheets of the absorbent unit is made of an essentially stretchable material. The object of the invention is to provide vertical force vectors which function to urge the absorbent unit against the crotch of the wearer, and inwardly directed, horizontal force vectors towards the wearer's hips such as to press the absorbent unit against the sides of the wearer.

The European Patent Application EP 0 412 549 A1 teaches an absorbent pants-type diaper which includes elastic inner and outer casing sheets or layers and an elastic barrier layer mounted between said casing sheets. The pants-type diaper also includes elastic elements at both the waist and the leg openings.

The U.S. Pat. No. 4,690,681 teaches a pants-type absorbent article that is intended for use with menstruation or mild incontinence. The absorbent pad is integrated with the article and the front and the back part of the article extend further up the body of the wearer than in the case of "normal" menstruation pads. On the other hand, the size of the absorbent pad is so restricted as to be considered unsuitable for use in absorbing larger quantities of urine. The absorbent pants include waist and leg elastic. The pants also include casing layers which are made of a stretchable material, for instance a mixture of nylon and cotton. The absorbent pad is located in an impermeable zone of the pants, between the side-pieces thereof. This impermeable zone includes non-stretchable material and the stretchability required to enable the pants to shape to the wearer's body is obtained totally from the stretchable material in the casing layers.

None of the aforementioned absorbent trouser diapers solves the problem of ensuring that the pants-type diapers will be capable of maintaining the absorbent pad in conforming abutment with the wearer's body and also of supporting the absorbent pad subsequent to the pad being filled with a large quantity of liquid.

Pants-type diapers which comprise casing layers that are made of stretchable material, such as the pants-type diapers taught by U.S. Pat. No. 4,205,679 and EP 0 412 549, are unsatisfactory because the casing layer in the crotch-part of the diaper in which the absorbent pad is located is also stretchable. Thus, the casing layer in the crotch-part of the diaper will stretch under the weight of the absorbent pad and the diaper will sag or hang like a sack between the legs of the wearer, that is if the diaper can be held-up at all. This is particularly disadvantageous when the casing layer is able to stretch in the longitudinal direction of the pants-type diapers, i.e. in a direction away from the waist part to the crotch-part of the diaper, since the force of gravity acts in this direction when the wearer stands upright, therewith increasing the strain on the casing layer in this direction.

Pants-type diapers which have solely elastically stretchable side-pieces or elastically stretchable casing layers in diaper parts other than those parts in which the absorbent pad is arranged, as taught by EP 0 320 991 and U.S. Pat. No. 4,690,681 respectively, also suffer drawbacks. The elastically stretchable parts of the casing layers of these diapers are not sufficiently effective to be able to hold the absorbent pad in against the wearer's body, above all the front-part of the absorbent pad against the wearer's stomach. Neither are the elastically stretchable side-pieces alone sufficiently active to be able to support the increase in load that results from the absorption of fluid by the absorbent pad. Neither are elastic elements that are mounted along the waist opening of the trouser diapers outside the end-edges of the absorbent pad satisfactory in holding the absorbent pad against the wearer's stomach or in supporting a liquid-filled absorbent pad.

SUMMARY OF THE INVENTION

The present invention, however, provides an absorbent pants-type diaper of the kind defined in the introduction which will effectively enable the diapers to lie sealingly against and shape conformingly to the wearer's body, while enabling the diapers to support an absorbent pad even when the pad is full of liquid. An inventive pants-type diaper is primarily characterized in that at least one of the front and the back parts of the diaper has at least one elastically stretchable region; in that the crotch-part is essentially non-stretchable in relation to said stretchable region; in that at least one of the respective end-parts of the absorbent pad is disposed within one of said elastically stretchable regions while the centre-part of the absorbent pad is disposed within the relatively non-stretchable crotch-part of the diaper, whereby those forces exerted by the elastically stretchable region on the end-part or end-parts of the absorbent pad will hold the absorbent pad in sealing abutment with the wearer's body when the trouser diaper is worn.

According to one embodiment of the invention, the stretchable region extends beyond the side-edges and end-edge of the front and/or the back end-part of the absorbent pad.

According to another embodiment, the stretchable region covers essentially the whole of the front-part and/or back-part.

According to a further embodiment of the invention, the stretchable region can stretch essentially in the transverse direction of the absorbent pad, but is essentially non-stretchable in the longitudinal direction of said pad.

The elastically stretchable region may, for instance, include elastically stretchable elements, e.g. elastically stretchable threads, bands, ribbons or the like which are mounted in a pre-stretched state, or an elastically stretchable material layer, for instance an elastically stretchable film, an elastically stretchable non-woven material, laminate, foamed material or the like.

According to another embodiment, the pants-type diaper includes elastically stretchable waist parts at the end-edge of the front and/or the back part at the waist opening of the diaper, said waist parts exhibiting a greater stretching and contraction force than the stretchable region in the front and/or the back part.

In the case of another embodiment of the invention, the elastically stretchable part at the waist opening includes an edge-part of the elastically stretchable material layer, said edge-part having at least twice the thickness of the remaining parts of said elastically stretchable material layer, as a result of folding the elastically stretchable material layer inwardly over itself at least once within said edge-part.

According to the present invention, the elastically stretchable region forms an elastically stretchable waist zone over the whole of or over parts of the front and/or the back parts of the diaper, said parts also extending over at least one end-part of the absorbent pad.

The elastic waist zone has an essentially greater extension in over the diaper in a direction from its end-edge than conventional, relatively narrow elastic elements mounted along the end-edge of the pants-type diaper. Furthermore, the elastic waist zone extends over the end-part or end-parts of the absorbent pad and not solely in the side-pieces externally of the side-edges of the absorbent pad, as in the case of the pants-type diaper taught by EP 0 320 991. In this way, there is obtained an elastically stretchable region in a waist zone which provides much better holding of the absorbent pad than that afforded by the earlier known solutions with elastic elements or side-pieces mounted outside the end-edges and side-edges of the absorbent pad.

The elastic waist zone of the inventive pants-type diaper is also highly significant in enabling the pants to remain in position on the wearer as the load increases. It is also important that the crotch-part of the diaper pants is essentially non-stretchable in comparison with the elastically stretchable waist zone. Thus, the casing layers within the crotch-part will not stretch under the weight of the liquid-filled absorbent pad, as is the case with the earlier known pants-type diapers that are comprised of totally stretchable casings.

According to one particularly advantageous embodiment of the invention, the elastic waist zone can stretch in the transverse direction of the absorbent pad, but is relatively non-stretchable in the longitudinal direction of said pad. This is advantageous, because it counteracts the tendency of the casing layer of the pants-type diaper to stretch in the longitudinal direction of the absorbent pad, such stretching otherwise resulting in greater risk that the diaper will sag or hang down between the legs of the wearer.

A particular advantage is obtained with an elastic waist zone which extends essentially over the full width of the front and the back parts, i.e. around the whole of the waist part formed by the diaper pants. This will increase the girth of the pants in comparison with pants provided solely with elastically stretchable side-pieces, which is important among other things in order to enable the waist opening to be widened when taking-off and putting-on the pants and to enable pants of one and the same size to fit users of different sizes, therewith restricting the number of pants-type diaper sizes to a minimum.

BRIEF DESCRIPTION OF THE DRAWINGS

The invention will now be described in more detail with reference to exemplifying embodiments thereof and also with reference to the accompanying drawings, in which.

DETAILED DESCRIPTION OF THE INVENTION

Figure 1:
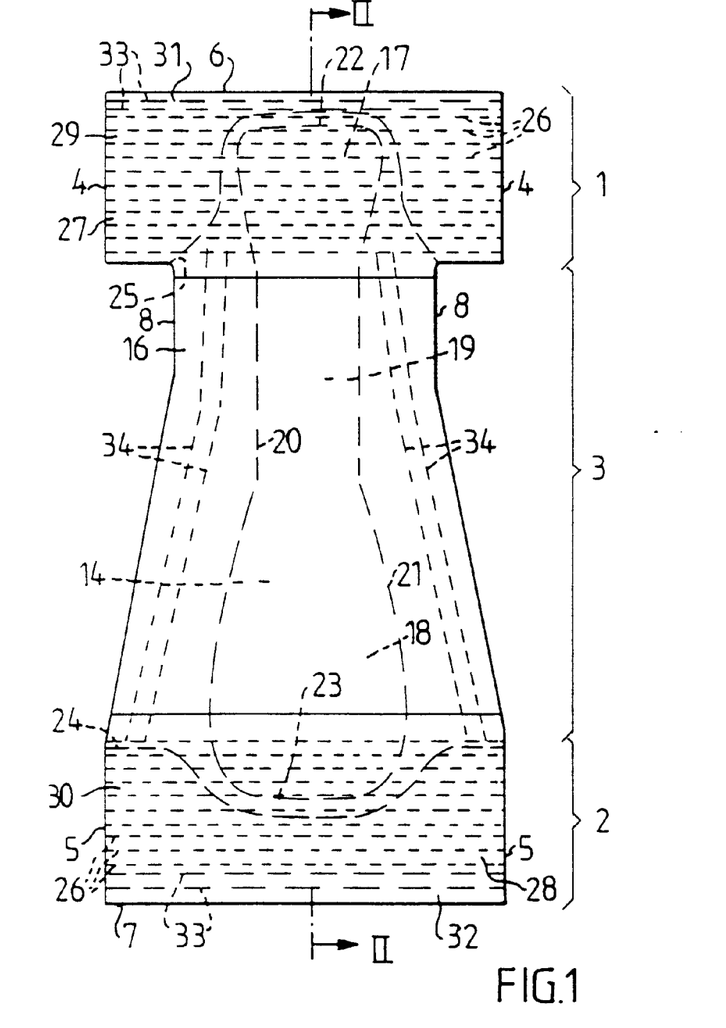
FIG. 1 illustrates schematically and from above an absorbent pants-type diaper constructed in accordance with the invention, with that side of the diaper that is intended to lie distal from the wearer facing towards the viewer, said diaper being shown in a state in which the front and the back parts thereof have still not yet been joined together to form waist and leg openings respectively, and in which the elastic elements of the diaper are in a stretched state.
Figure 3:
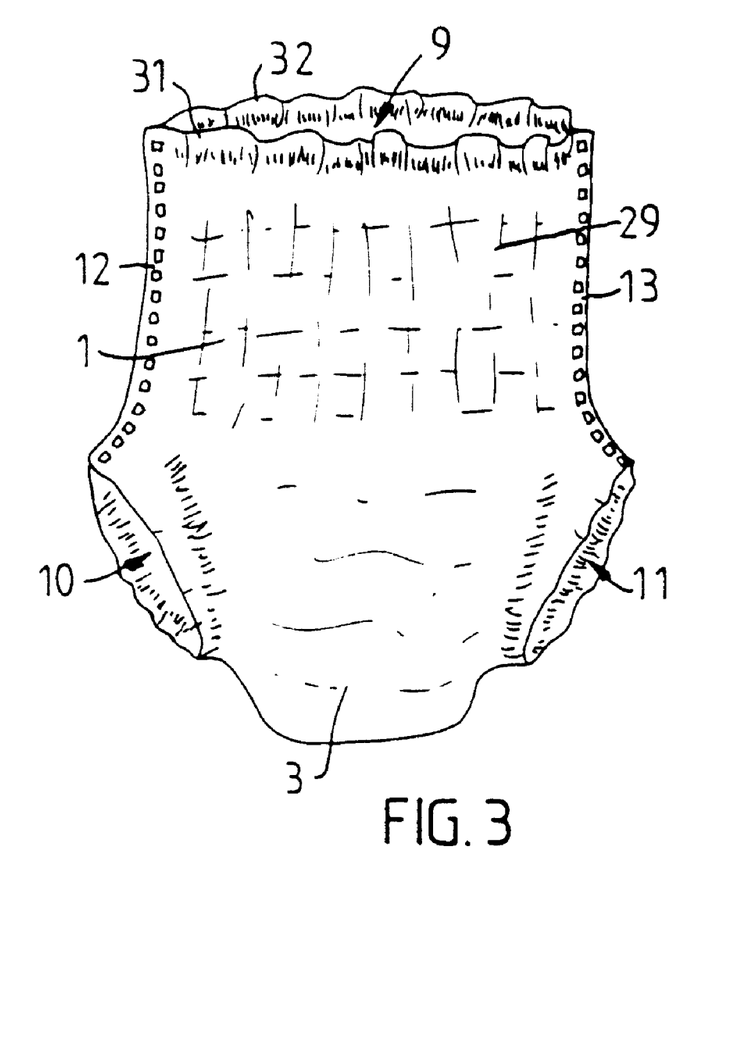
FIG. 3 is a front view which illustrates the pants-type diaper in an assembled state.

FIG. 1 illustrates an absorbent pants-type diaper in an unassembled state, i.e. a state in which the waist and leg openings of the pants have not yet been formed. The pants-type diaper includes a front-part 1, which is intended to be placed forwardly on the wearer, a back-part 2, which is intended to be placed rearwardly on the wearer, and a crotch-part 3 which is located between the front and the back parts 1, 2 and which is intended to be placed between the thighs of the wearer. No precise limits can be drawn between the respective parts and the size relationships therebetween can vary, and consequently the division illustrated in FIG. 1 can only be seen as a schematic example. Each of the front and the back parts have two side-edges 4, 5 and one end-edge 6, 7. The crotch-part 3 has two side-edges 8. As will be seen from FIG. 3, when the pants-type diaper is in its assembled or ready-to-wear state, the diaper has a waist opening 9 between respective end-edges 6, 7 of the front and the back parts, and two leg openings 10, 11 which are surrounded by respective side-edges 8 of the crotch-part. Respective side-edges 4 of the front-part are joined to corresponding respective side-edges 5 of the back-part, such that the pants-type diaper will present two side-closure parts 12, 13 which extend from the waist opening 9 to respective leg openings 10, 11. on respective sides of the diaper. The side closures may be obtained with the aid of heat-sealing, ultrasonic-welding, gluing or sewing techniques or some other suitable conventional technique.

Figure 2:
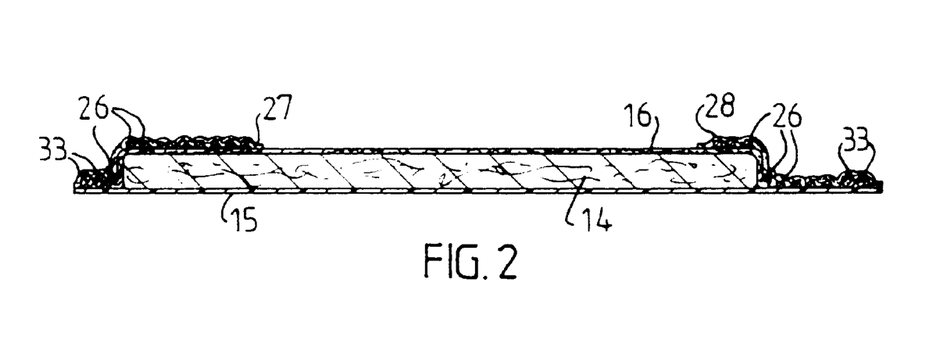
FIG. 2 is a sectional view taken on the line II—II in FIG. 1.

It will be seen from FIGS. 1 and 2 that the pants-type diaper includes an elongated absorbent pad 14 which extends in the longitudinal direction of the diaper and which is enclosed between an inner casing layer 15 and an outer casing layer 16, with the latter layer facing towards viewer of FIG. 1. The inner casing layer 15 is placed on that side of the absorbent pad 14 which faces towards the wearer in use and is liquid-permeable and comprised, for instance, of a non-woven material. The fibers may be comprised, for instance, of polyethylene, polypropylene, polyester or mixtures thereof. They may also be comprised of viscose fibers. It is also conceivable for the inner casing layer 15 to be comprised of a perforated plastic sheet, for instance perforated polyethylene film or the like. The outer casing layer or backing sheet 16 is liquid-impermeable or at least hydrophobic and may, for instance, be comprised of a sheet of polyethylene or a non-woven material which has been coated or laminated with polyolefins for instance, so as to become liquid-impermeable or at least hydrophobic.

The absorbent material in the absorbent pad 14 may, for instance, comprise cellulose fibers. The material may also include other absorbents, such as polymeric hydrocolloidal material, for instance in particle form. Such materials are normally referred to as superabsorbents, by which is meant materials whose liquid absorbing capacity is equal to many times their own weight. The absorbent pad may also include non-absorbent material, for instance thermoplastic melt fibers, with the intention of strengthening the absorbent pad. Although the absorbent pad 14 shown in FIG. 2 has only one single layer, it will be understood that the absorbent pad may conceivably comprise more than one layer.

The illustrated absorbent pad 14 also has a front end-part 17, a rear end-part 18, an intermediate centre-part 19, two side-edges 20, 21 and two end-edges 22, 23. The absorbent pad 14 is essentially rectangular in shape, although the two end-parts 17, 18 are slightly wider than the centre-part 19. The absorbent pad, however, is not restricted to the shape illustrated in FIG. 1, and other shapes, such as hourglass shapes or T-shapes are conceivable.

The extension of the inner casing layer 15 is equally as large as the extension of the pants-type diaper. The absorbent pad 14 is narrower and shorter than the inner casing layer 15 and is displaced slightly forwards in the diaper, wherein the front end-part 17 of the absorbent pad is located in the front-part 1 of the diaper, the centre-part 19 of the absorbent pad is located in the crotch-part 3 of the diaper and the rear end-part 18 of the absorbent pad has parts located in both the crotch-part 3 of the diaper and in the back-part 2. The front end-edge 22 of the absorbent pad is disposed closer to the front end-edge 6 of the diaper than the rear and-edge 7 is disposed relative to the rear end-edge 23 of the absorbent pad. Naturally, other variants are conceivable. For instance, the absorbent pad may extend essentially along the whole length of the diaper, or alternatively no part of the absorbent pad may be disposed in the back-part at all, when, in the former case, it is desired to increase the size of the absorbent pad or, in the latter case, when wishing to produce a more airy diaper. The outer casing layer 16 does not have the same longitudinal extension as the inner casing layer 15, and the rear end-edge of the outer casing layer, indicated by the broken line 24, terminates just short of the rear end-edge 23 of the absorbent pad. Furthermore, the outer casing layer 16 in the rear-part 2 of the diaper only extends laterally through a small distance outside the side-edges 20, 21 of the absorbent pad. Neither does the outer casing layer 16 in the front-part 1 of the diaper pants extend laterally and longitudinally to the same extent as the inner casing layer 15, but solely extends through a short distance beyond the front end-edge 22 and the side-edges 20, 21 of the absorbent pad, as indicated by the broken line 25 in FIG. 1. This means that large parts of the back-part 2 and the front-part 1 of the diaper pants will not be covered by the outer casing layer 16, thereby facilitating the passage of air through the diaper casing within these parts. Naturally, the outer casing layer 16 may also have an extension which coincides essentially with the extension of the inner casing layer 15, when wishing to improve protection against leakage over essentially the whole of the surface of the casing layers, in which case the outer casing layer 16 is preferably made permeable to both air and vapour.

A plurality of transverse elastic elements 26, for instance elastic threads, bands, ribbons or the like, are mounted in a pre-stretched state transversely over the front-part 1 and the rear-part 2. The number of elastic elements provided is not restricted to the number shown in FIG. 1, and the number of elements 26 may be more or less than that shown. In the front and the back parts 1 and 2, respective layers 27 and 28 of textile-like material, for instance non-woven material, are placed outermost on the diaper. The elastic threads 26 are mounted between these layers 27, 28 and the outer casing layer 16 and the inner casing layer 15 within those parts of the front and back parts in which the outer casing layer 16 does not extend. The back layer 28 and also the front layer 27 thus extend slightly in over the rear end-edge 23 and the front end-edge 22 of the absorbent pad, said layers also covering a piece of the outer casing layer 16. Instead of two separate textile-like layers, it is conceivable to apply one single textile-like layer over the whole of the diaper, this layer similarly covering the elastic elements 26 and also the whole of the outer casing layer 16.

Thus, the front and the back parts 1, 2 of the diaper pants will have regions 29, 30 which are elastically stretchable essentially in the transverse direction of the diaper and which, in the FIG. 1 embodiment, coincide essentially with the front and the back parts 1, 2. Instead of elastic bands, ribbons, threads or the like, it is conceivable for the stretchable regions 29, 30 to comprise an elastically stretchable material, for instance an elastically stretchable film, an elastically stretchable non-woven material, laminate, foamed material or the like. An elastically stretchable film may, for instance, include ethylene vinyl acetate, ethylene acrylic acid, ethylene butyl acetate, polyurethane, styrene butadiene, polybutadiene, polyisoprene, isoprene rubber or ethylene propylene rubber. A similar elastically stretchable material may also be disposed so that the elastically stretchable regions 29, 30 are essentially stretchable solely in the transverse direction of the diaper.

The aforesaid elements 26 or said materials are joined with at least a respective one of the inner or outer casing layers 15, 16 or respective textile-like layers 27, 28 in respective elastically stretchable regions 29, 30, at least in discrete regions.

The pants-type diaper also has elastically stretchable front and back waist parts 31, 32 along the front and the rear end-edge 6, 7 of the diaper respectively. Two elastic elements 33 are mounted along respective end-edges 6, 7 within respective waist parts 31, 32. These elastic elements 33 may also be fewer or more than two in number. The elastic elements 33 may be comprised of elastic threads, bands, ribbons or the like mounted in a pre-stretched state. The elastic elements 33 in the waist parts 31, 32 may also exhibit greater stretching and contraction power than the individual elastic elements 26 in the aforesaid elastically stretchable regions 29, 30. For instance, the elastic elements 33 in the waist parts 31, 32 may be comprised of broad and strong bands, whereas the elastic elements 26 in the elastically stretchable regions 29, 30 may be comprised of thin threads.

Figure 4:
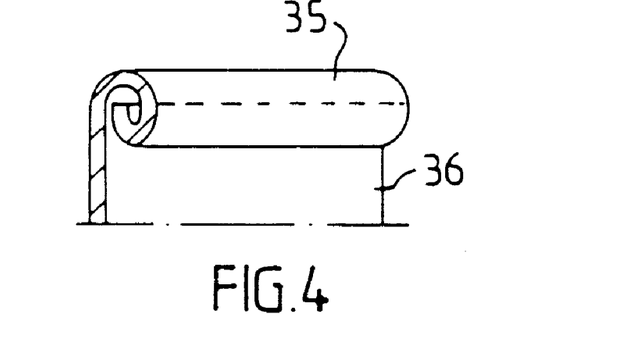
FIG. 4 is a perspective view of a simplified embodiment of a waist part of pants-type diapers in accordance with another embodiment of the invention.

As an alternative to threads or bands, it is conceivable to use elastic films, laminates, non-woven material, foamed material or like material also in the waist parts 31, 32. For instance, in this regard, it is possible to use the same elastic film which forms, at the same time, elastic elements within the stretchable regions 29, 30. FIG. 4 illustrates a simplified embodiment in which one edge-part 35 of an elastically stretchable film 36 has been folded in over itself, so as to obtain triple film thickness within the aforesaid edge-part 35. In the case of the embodiment illustrated in FIGS. 1–3, this edge-part 35 may be included in the elastically stretchable waist part 21, 32 at the waist opening 9 of the diaper pants, while remaining parts of the film 36 are included in the elastically stretchable region in the front-part 1 and/or the back-part 2.

The pants-type diapers also include other elastically stretchable elements 34, preferably in the form of elastically stretchable bands, ribbons, threads or the like which are mounted in a pre-stretched state along the respective side-edges 8 of the crotch-part of the diaper, from a border region between the front-part 1 and the crotch-part 3 to a border region between the back-part 2 and the crotch-part 3. In the FIG. 1 embodiment, the aforesaid other elastically stretchable elements 34 are two in number along respective side-edges 8, although this number may equally as well be greater and fewer than two. The aforesaid further elastic elements 34 exhibit in a direction towards the front-part 1 a successively decreasing distance between two elements 34 mounted on respective sides of the absorbent pad 14.

It will be understood, however, that the aforesaid further elastically stretchable elements 34 may be disposed in any other pattern whatsoever, for instance they may be disposed generally parallel with the longitudinal direction of the absorbent pad.

The invention shall not be considered restricted to the illustrated exemplifying embodiments thereof, since several variations are conceivable within the scope of the following claims.

What is claimed is:

1. In an absorbent pants-type diaper which is intended for one-time use only and which comprises:
   a front part having side edges and an end edge;
   a back part having side edges and an end edge;
   a crotch part between the front and back parts;
   at least two side-closure parts which mutually join parts of the side-edges of respective front and back parts, so that the pants-type diaper will present a waist opening and two leg openings;
   an elongated absorbent pad comprising at least one absorbent layer having a front and a rear end part and an intermediate central part;
   an inner casing layer placed on that side of the absorbent layer which is intended to face towards a wearer; and
   an outer casing layer which is placed on the other side of the absorbent layer, the improvement wherein the pants-type diaper further comprises at least one elastically stretchable region covering essentially the whole of at least one of the respective front and back parts; the crotch part being essentially non-stretchable in relation to said stretchable region; at least one of the respective end parts of the absorbent layer being disposed within one of said elastically stretchable regions; the central part of the absorbent layer being disposed within the relatively non-stretchable crotch part of the diaper; and at least one of the stretchable regions being disposed on the side of the absorbent layer facing away from the inner casing layer, whereby those forces that are exerted by the elastically stretchable region on at least one of the end part of the absorbent layer function to hold the absorbent layer in sealing abutment with the wearer when the pants-type diaper is worn.

2. The pants-type diaper according to claim 1, wherein the stretchable region extends beyond the side edges and the end edge of at least one of the front and back end parts of the absorbent layer.

3. The pants-type diaper according to claim 1, wherein the stretchable region is stretchable essentially in the transverse direction of the absorbent pad but is essentially non-stretchable in the longitudinal direction of said pad.

4. The pants-type diaper according to claim 1, wherein the stretchable region includes elastically stretchable elements which are mounted in a pre-stretched state.

5. The pants-type diaper according to claim 4, wherein the elastically stretchable elements are joined with at least one of the casing layers at least in separate regions.

6. The pants-type diaper according to claim 5, wherein the stretchable elements of the stretchable region are applied to the outside of the outer casing layer and are covered by at least one additional outer casing layer of textile-like material.

7. The pants-type diaper according to claim 1, wherein the stretchable region includes an elastically stretchable material layer.

8. The pants-type diaper according to claim 7, wherein the elastically stretchable material layer is joined with at least one of the casing layers at least in separate regions.

9. The pants-type diaper according to claim 8, wherein the elastically stretchable material layer is applied to the outside of the outer casing layer and is covered by at least one additional outer casing layer of textile-like material.

10. The pants-type diaper according to claim 1, wherein at least one of the end edge of the front and the back parts has at the waist opening at least one elastically stretchable waist part whose stretching and contraction power is greater than the remainder of the stretchable region.

11. The pants-type diaper according to claim 10, wherein the elastically stretchable waist part at the waist opening includes elastically stretchable elements which are mounted in a pre-stretched state.

12. The pants-type diaper according to claim 10, wherein the stretchable region includes an elastically stretchable material layer, and the elastically stretchable waist part at the waist opening includes an edge-part of the elastically stretchable material layer, said edge-part having a thickness which is at least twice the thickness of the remaining parts of said elastically stretchable material layer, by virtue of being folded in over itself at least once within said edge-part.

13. The pants-type diaper according to claim 1, further including elastically stretchable elements mounted in a pre-stretched state, and disposed along side-edges of the diaper, at least within the crotch part, so that the distance between two elastically stretchable elements mounted on respective side-edges of the diaper will decrease successively in a direction towards said front-part.

14. The pants-type diaper according to claim 1, wherein the outer casing layer is liquid-impermeable; the outer casing layer in the front and the back part extending only slightly beyond edges of the absorbent pad; and portions of the front and the back parts which lie outside the outer casing layer are comprised of at least one of liquid-permeable and air-permeable material.

15. In an absorbent pants-type diaper which is intended for one-time use only and which comprises:
   a front part having side edges and an end edge;
   a back part having side edges and an end edge;
   a crotch part between the front and back parts;
   at least two side-closure parts which mutually join parts of the side-edges of respective front and back parts, so that the pants-type diaper will present a waist opening and two leg openings;
   an elongated absorbent pad comprising at least one absorbent layer having a front and a rear end part and an intermediate central part;
   an inner casing layer placed on that side of the absorbent layer which is intended to face towards a wearer; and
   an outer casing layer which is placed on the other side of the absorbent layer, the improvement wherein at least one of the respective front and back parts has at least one elastically stretchable region; the crotch part being essentially non-stretchable in relation to said stretchable region; at least one of the respective end parts of the absorbent layer being disposed within one of said elastically stretchable regions; the central part of the absorbent layer being disposed within the relatively non-stretchable crotch part of the diaper; at least one of the stretchable regions being disposed on the side of the absorbent layer facing away from the inner casing layer, whereby those forces that are exerted by the elastically stretchable region on at least one of the end part of the absorbent layer function to hold the absorbent layer in sealing abutment with the wearer when the pants-type diaper is worn; and at least one of the end edge of the front and the back parts has at the waist opening of the pants at least one elastically stretchable waist part whose stretching and contraction power is greater than the remainder of the stretchable region.

16. The pants-type diaper according to claim 15, wherein the stretchable region extends beyond the side edges and the end edge of at least one of the front and back end parts of the absorbent layer.

17. The pants-type diaper according to claim 16, wherein the stretchable region covers essentially the whole of at least one of the respective front and back parts.

18. The pants-type diaper according to claim 15, wherein the stretchable region is stretchable essentially in the transverse direction of the absorbent pad but is essentially non-stretchable in the longitudinal direction of said pad.

19. The pants-type diaper according to claim 15, wherein the stretchable region includes elastically stretchable elements which are mounted in a pre-stretched state.

20. The pants-type diaper according to claim 19, wherein the elastically stretchable elements are joined with at least one of the casing layers at least in separate regions.

21. The pants-type diaper according to claim 20, wherein the stretchable elements of the stretchable region are applied to the outside of the outer casing layer and are covered by at least one additional outer casing layer of textile-like material.

22. The pants-type diaper according to claim 15, wherein the stretchable region includes an elastically stretchable material layer.

23. The pants-type diaper according to claim 22, wherein the elastically stretchable material layer is joined with at least one of the casing layers at least in separate regions.

24. The pants-type diaper according to claim 23, wherein the elastically stretchable material layer is applied to the outside of the outer casing layer and is covered by at least one additional outer casing layer of textile-like material.

25. The pants-type diaper according to claim 15, wherein the elastically stretchable waist part at the waist opening includes elastically stretchable elements which are mounted in a pre-stretched state.

26. The pants-type diaper according to claim 15, wherein the stretchable region includes an elastically stretchable material layer, and the elastically stretchable waist part at the waist opening includes an edge-part of the elastically stretchable material layer, said edge-part having a thickness which is at least twice the thickness of the remaining parts of said elastically stretchable material layer, by virtue of being folded in over itself at least once within said edge-part.

27. The pants-type diaper according to claim 15, further including elastically stretchable elements mounted in a pre-stretched state, and disposed along side-edges of the diaper, at least within the crotch part, so that the distance between two elastically stretchable elements mounted on respective side-edges of the diaper will decrease successively in a direction towards said front-part.

28. The pants-type diaper according to claim 15, wherein the outer casing layer is liquid-impermeable; the outer casing layer in the front and the back part extending only slightly beyond edges of the absorbent pad; and portions of the front and the back parts which lie outside the outer casing layer are comprised of at least one of liquid-permeable and air-permeable material.

* * * * *

(12) EX PARTE REEXAMINATION CERTIFICATE (5730th)
United States Patent
Widlund et al.

(10) Number: US 6,375,646 C1
(45) Certificate Issued: Mar. 27, 2007

(54) ABSORBENT PANTS-TYPE DIAPER

(75) Inventors: Urban Widlund, Mölnlycke (SE); Gunilla Hedlund, Ljungskile (SE); Robert Kling, Skene (SE)

(73) Assignee: SCA Hygiene Products AB, Gothenburg (SE)

Reexamination Request:
No. 90/007,112, Jul. 7, 2004

Reexamination Certificate for:
Patent No.: 6,375,646
Issued: Apr. 23, 2002
Appl. No.: 08/295,874
Filed: Sep. 6, 1994

(22) PCT Filed: Mar. 1, 1993

(86) PCT No.: PCT/SE93/00176
§ 371 (c)(1),
(2), (4) Date: Sep. 6, 1994

(87) PCT Pub. No.: WO93/17648
PCT Pub. Date: Sep. 16, 1993

(30) Foreign Application Priority Data
Mar. 4, 1992 (SE) .............................. 9200663

(51) Int. Cl.
*A61F 13/15* (2006.01)

(52) U.S. Cl. ............................... 604/385.3; 604/385.22
(58) Field of Classification Search ................. None
See application file for complete search history.

(56) References Cited

U.S. PATENT DOCUMENTS 4,430,086 A * 2/1984 Repke ................... 604/385.26
4,586,199 A   5/1986 Birring
4,756,709 A * 7/1988 Stevens ................. 604/385.22
4,762,521 A * 8/1988 Roessler et al. ....... 604/385.26
4,936,840 A   6/1990 Proxmire
5,004,466 A * 4/1991 Uda et al. .............. 604/385.24
5,415,649 A   5/1995 Watanabe et al.

FOREIGN PATENT DOCUMENTS

| EP | 0 187 727 | 7/1986 |
|----|-----------|--------|
| EP | 0 487 921 | 6/1992 |
| FR | 0 211 197 | 2/1987 |
| GB | 2253131 A * | 9/1992 |

OTHER PUBLICATIONS

Applicant's translation of Japanese Patent Kokai No. 205053/91, received during prosecution of U.S. Appl. No. 08/295,874, now Pat 6,375,646.*

European Opposition Proceeding report of Feb. 25, 2000 for EP–B–0630221.*

* cited by examiner

*Primary Examiner*—Michael O'Neill (57) ABSTRACT

A disposable, absorbent pants-type diaper includes a front-part (1), a back-part (2), a crotch-part (3) between the front and back parts (1, 2), at least two side-closure parts (12, 13) which mutually join parts of the side-edges (4, 5) of respective front and back parts, so that the pants will present a waist opening (9) and two leg openings (10, 11). The diaper pants further include an elongated absorbent pad (14), an inner casing layer (15), and an outer casing layer (16). At least one of the respective front and back parts (1, 2) has at least one elastically stretchable region (29, 30). The crotch-part (3) is essentially non-stretchable in relation to the stretchable region (29, 30). At least one of respective end-parts (17, 18) of the absorbent pad (14) is disposed within one of the elastically stretchable regions (29, 30), while the center-part (19) of the absorbent pad is disposed within the relatively non-stretchable crotch-part (3) of the pants.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–28 is confirmed.

New claims 29–38 are added and determined to be patentable.

29. *The pants-type diaper according to claim 1, wherein the pants-type diaper comprises two elastically stretchable regions covering essentially the whole of each of the respective front and back parts.*

30. *The pants-type diaper according to claim 29, wherein the end edge of the front part has at the waist opening an elastically stretchable waist part whose stretching and contraction power is greater than the remainder of the stretchable region of the front part and wherein the end edge of the back part has at the waist opening an elastically stretchable waist part whose stretching and contraction power is greater than the remainder of the stretchable region of the back part.*

31. *The pants-type diaper according to claim 15, wherein the pants-type diaper comprises two elastically stretchable regions covering essentially the whole of each of the respective front and back parts.*

32. *The pants-type diaper according to claim 31, wherein the end edge of the front part has at the waist opening an elastically stretchable waist part whose stretching and contraction power is greater than the remainder of the stretchable region of the front part and wherein the end edge of the back part has at the waist opening an elastically stretchable waist part whose stretching and contraction power is greater than the remainder of the stretchable region of the back part.*

33. *The pants-type diaper according to claim 31, wherein both of the respective end parts of the absorbent layer are disposed within said elastically stretchable regions.*

34. *The pants-type diaper according to claim 15, wherein the at least one elastically stretchable waist part extends over at least one end-part of the absorbent pad.*

35. *The pants-type diaper according to claim 1, wherein the at least one elastically stretchable region covering essentially the whole of at least one of the respective front and back parts includes a plurality of spaced apart elastically stretchable elements,*

*wherein the at least one elastically stretchable region covering essentially the whole of at least one of the respective front and back parts comprises a first portion having at least one elastically stretchable element and a second portion having at least one elastically stretchable element, and*

*wherein the at least one of the respective end parts of the absorbent layer being disposed within the at least one elastically stretchable region covering essentially the whole of at least one of the respective front and back parts is disposed within the first portion, and is not disposed within the second portion.*

36. *The pants-type diaper according to claim 35, wherein the plurality of spaced apart elastically stretchable elements are elastically stretchable threads.*

37. *The pants-type diaper according to claim 17, wherein the at least one elastically stretchable region covering essentially the whole of at least one of the respective front and back parts includes a plurality of spaced apart elastically stretchable elements,*

*wherein the at least one elastically stretchable region covering essentially the whole of at least one of the respective front and back parts comprises a first portion having at least one elastically stretchable element and a second portion having at least one elastically stretchable element, and*

*wherein the at least one of the respective end parts of the absorbent layer being disposed within the at least one elastically stretchable region covering essentially the whole of at least one of the respective front and back parts is disposed within the first portion, and is not disposed within the second portion.*

38. *The pants-type diaper according to claim 37, wherein the plurality of spaced apart elastically stretchable elements are elastically stretchable threads.*

\* \* \* \* \*